(12) United States Patent
Green et al.

(10) Patent No.: US 10,940,159 B2
(45) Date of Patent: Mar. 9, 2021

(54) COMBINATION IMMEDIATE/DELAYED RELEASE DELIVERY SYSTEM FOR SHORT HALF-LIFE PHARMACEUTICALS INCLUDING REMOGLIFLOZIN

(76) Inventors: James Trinca Green, Raleigh, NC (US); William Owen Wilkison, Raleigh, NC (US)

(*) Notice: Subject to any disclaimer, the term of this patent is extended or adjusted under 35 U.S.C. 154(b) by 1177 days.

(21) Appl. No.: 13/809,222

(22) PCT Filed: Jul. 7, 2011

(86) PCT No.: PCT/US2011/043143
§ 371 (c)(1),
(2), (4) Date: Mar. 19, 2013

(87) PCT Pub. No.: WO2012/006398
PCT Pub. Date: Jan. 12, 2012

(65) Prior Publication Data
US 2013/0209563 A1    Aug. 15, 2013

Related U.S. Application Data

(60) Provisional application No. 61/362,946, filed on Jul. 9, 2010.

(51) Int. Cl.
| | |
|---|---|
| A61K 31/7056 | (2006.01) |
| A61K 9/20 | (2006.01) |
| A61K 9/24 | (2006.01) |
| A61K 9/50 | (2006.01) |
| A61K 45/06 | (2006.01) |

(52) U.S. Cl.
CPC .......... *A61K 31/7056* (2013.01); *A61K 9/209* (2013.01); *A61K 9/2077* (2013.01); *A61K 9/5084* (2013.01); *A61K 45/06* (2013.01)

(58) Field of Classification Search
CPC .................................................. A61K 31/7056
See application file for complete search history.

(56) References Cited

U.S. PATENT DOCUMENTS

| | | | |
|---|---|---|---|
| 5,985,843 A * | 11/1999 | Higo | ...................... A61K 9/209 514/25 |
| 6,589,553 B2 | 7/2003 | Li et al. | |
| 6,660,300 B1 | 12/2003 | Timmins et al. | |
| 7,488,498 B2 | 2/2009 | Makino et al. | |
| 2002/0132001 A1 | 9/2002 | Garthwaite et al. | |
| 2003/0137067 A1 | 7/2003 | Cooper et al. | |
| 2004/0005358 A1 | 1/2004 | Slugg et al. | |
| 2004/0242640 A1 | 12/2004 | Desai et al. | |
| 2008/0026060 A1 | 1/2008 | Zerbe et al. | |
| 2008/0279934 A1 | 11/2008 | Soennichsen et al. | |
| 2008/0305165 A1 | 12/2008 | Noh et al. | |
| 2010/0029486 A1 | 2/2010 | Willis et al. | |

FOREIGN PATENT DOCUMENTS

| | | | |
|---|---|---|---|
| EP | 1 354 888 A1 | 10/2003 | |
| JP | 2009-511441 A | 3/2009 | |
| JP | 2010-510241 A | 4/2010 | |
| WO | 2001/047557 A1 | 7/2001 | |
| WO | 2005/046684 A1 | 5/2005 | |
| WO | WO 2007083323 A2 * | 7/2007 | ........... A61K 9/1617 |
| WO | 2008/061226 A3 | 5/2008 | |
| WO | 2008/128086 A1 | 10/2008 | |
| WO | 2010/045656 A2 | 4/2010 | |
| WO | 2012/006398 A2 | 1/2012 | |

OTHER PUBLICATIONS

Oxford English Dictionary, "disperse, v.", OED Online, Oxford University Press, 6 pages, accessed Mar. 10, 2016, available at http://www.oed.com/view/Entry/55006?result=2&rskey=cdfb5C&&print (Mar. 2016).*
Extended European search report dated Oct. 15, 2013, in EP Application No. 11804320.7.
English translation of JP Office Action, dated Apr. 23, 2015.

* cited by examiner

*Primary Examiner* — Dennis J Parad
(74) *Attorney, Agent, or Firm* — J.A. Lindeman & Co., PLLC

(57) ABSTRACT

A combination immediate/delayed release delivery system for compounds which have short half-life's, such as the antidiabetic remogliflozin etabonate, is provided which provides a dosage form that has two distinct phases of release, a formulation that promotes immediate release of the compound upon ingestion and another formulation which delays the release of the compound so that a dosing regimen of remogliflozin etabonate, once daily, may be achieved while providing effective control of plasma glucose and minimizing the nighttime exposure of this compound. The delivery system includes, but is not limited to, a combination of enteric coating of an immediate release formulation such that a delay in release is provided. Methods for forming the so-described immediate/delayed release delivery system and using such delivery system for treating diabetes are also provided.

9 Claims, 2 Drawing Sheets

COMBINATION IMMEDIATE/DELAYED RELEASE DELIVERY SYSTEM FOR SHORT HALF-LIFE PHARMACEUTICALS INCLUDING REMOGLIFLOZIN

BACKGROUND OF THE INVENTION

The prevalence of diabetes has become an increasing concern to the world's population. In 2007, approximately 246 million people were affected by the disease, with an additional 7 million people developing the disease each year. It is estimated that by 2025, 380 million people will have diabetes.

Diabetes is a metabolic syndrome characterized by hyperglycemia, which results from an absolute deficiency in insulin secretion (type 1 diabetes) or from resistance to insulin action combined with an inadequate compensatory increase in insulin secretion (type 2 diabetes). Chronic hyperglycemia is a major risk factor for micro vascular complications such as retinopathy, nephropathy, and neuropathy. If attempts to adopt a healthier lifestyle fail to achieve and maintain target glycemic levels, additional therapies are required.

SUMMARY OF THE INVENTION

The present invention relates to a new dosage form for short half-life medicaments, such as the antidiabetic remogliflozin etabonate, which provides for an immediate release of the drug and also for a delayed release of a second bolus of drug, so that a dosing regimen of at least 250 mg remogliflozin etabonate once daily, may be achieved while providing effective control of plasma glucose, and to a method for treating diabetes employing such dosage form.

ABBREVIATIONS

Figure 1:
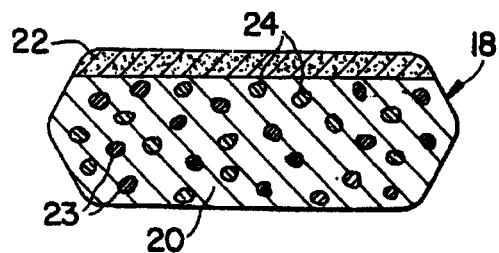
FIG. 1 is a cross sectional representation of a tablet of the pharmaceutical composition described herein.

| | |
|---|---|
| SGLT (sodium glucosecotransporter) | A1C (Hemoglobin A1C) |
| UKPDS (United Kingdom Prospective Diabetes Study) | HDL (high density lipoprotein) |
| ADA(American Diabetes Association) | QD (once daily) |
| BID (twice daily) | T2DM (type 2 diabetes mellitus) |
| GI (gastrointestinal) | GLP-1 (glucagon-like peptide-1) |
| DPP-IV (dipeptidyl protease IV) | HMG CoA(3-Hydroxy-3-methyl-glutaryl CoEnzyme A) |
| ACAT (acyl-CoA:cholesterol O-acyl transferase) | |
| LHRH (Lutenizing Hormone Releasing Hormone) | |
| AUC (area under the curve) | IR (immediate release) |
| MR (modified/sustained release) | MTP (Microsomal Triglyceride Transfer) |
| FPG (Fasting Plasma Glucose) | |

Diabetes

Attention has recently focused on the potential of sodium glucose cotransporter 2 (SGLT2) as new drug targets for the treatment of diabetes (1). The SGLT family consists of several isoforms that actively transport glucose and galactose across intestinal and renal membranes, a process that is coupled with sodium ion transport (2). SGLT2 is a low affinity, high capacity sodium-glucose cotransporter located mainly in the S1 segment of the proximal tubule of the kidney (3). In a healthy person, greater than 99% of the plasma glucose filtered in the kidney is reabsorbed. SGLT2 facilitates approximately 90% of this reabsorption. The remaining 10% is likely mediated by SGLT1, a high-affinity cotransporter located in the intestines and the renal proximal tubule. Humans with inactivating SGLT2 mutations exhibit persistent renal glucosuria but are otherwise healthy (4,5). Therefore, inhibition of SGLT2 appears to be an attractive way to improve glucose homeostasis. SGLT2 inhibition is expected to clear glucose from the bloodstream by increasing urinary glucose excretion, a mechanism that does not require insulin secretion from marginally functioning pancreatic beta cells.

Ideally, the inhibition of this glucose transporter should occur during the postprandial glucose excursion phase, where glucose enters into the blood after a meal. In healthy, nondiabetic subjects, 2-h postprandial blood glucose levels are usually <120 and rarely >140 mg/dl. Glucose levels peak at ~1 h after the start of the meal and then return to preprandial levels within 2-3 h (6,7). This rise and fall of postprandial glucose levels is mediated by the first-phase insulin response, in which large amounts of endogenous insulin are released, usually within 10 min, in response to nutrient intake. In individuals with type 2 diabetes, the first-phase insulin response is severely diminished or absent, resulting in persistently elevated postprandial glucose throughout most of the day (8).

To answer the question if targeting postprandial hyperglycemia improve overall glycemic control, in a study of patients with type 2 diabetes with secondary failure of sulfonylurea therapy, Feinglos et al. (9) showed that improvement of postprandial hyperglycemia, using insulin lispro (Humalog) at mealtime in combination with a sulfonylurea, not only reduced 2-h postprandial glucose excursions, but also reduced both fasting glucose and A1C levels from 9.0% to 7.1% (P<0.0001). Subjects in the lispro group also benefited from significantly decreased total cholesterol levels and improved HDL cholesterol concentrations.

Improvements in A1C levels were also reported in a study by Bastyr et al (10) which showed that therapy focused on lowering postprandial glucose versus fasting glucose may be better for lowering glycated hemoglobin levels. Further, in a study of patients with gestational diabetes, De Veciana et al (11) demonstrated that targeting treatment to 1-h postprandial glucose levels rather than fasting glucose reduces glycated hemoglobin levels and improves neonatal outcomes.

There is continuing debate about whether and to what degree postprandial glucose contributes to the development of microvascular and macrovascular complications. The report from the ADA consensus conference on postprandial glucose reiterated findings from the Diabetes Control and Complications Trial, the Kumamoto study, and the UKPDS, which demonstrated that therapies directed at achieving normal glycemia reduce the development and delay the progression of long-term microvascular complications (12). Further, as mentioned earlier, epidemiological analysis of UKPDS data showed that macrovascular outcomes were also improved by lowering glycemic levels (13). Therefore, if postprandial glucose is a contributor to overall glycemia, then postprandial glucose control must be a contributor to the development of diabetes complications.

Numerous epidemiological studies have shown elevated postprandial/post-challenge glucose to be independent and significant risk factors for macrovascular complications and increased mortality risk. The Honolulu Heart Study (14) found a strong correlation between postchallenge glucose levels and the incidence of cardiovascular mortality. The Diabetes Intervention Study (15), which followed newly diagnosed patients with type 2 diabetes, found moderate postprandial hyperglycemia to be more indicative of artherosclerosis than was fasting glucose, and found postprandial but not fasting glucose to be an independent risk factor for cardiovascular mortality. The DECODE Study (16) which followed more than 25,000 subjects for a mean period of 7.3 years, showed that increased mortality risk was much more closely associated with 2-h post-glucose load plasma levels than with fasting plasma glucose. Similar to these findings, de Vegt et al (17) found that the degree of risk conferred by the 2-h postprandial glucose concentration was nearly twice that conferred by A1C level.

The safety of postprandial glucose control is both dependent upon the therapy used and specific to each patient's ability to recognize and treat hypoglycemia when it does occur. Although severe hypoglycemia is rare in patients with type 2 diabetes, fear of hypoglycemia (among patients and providers) remains a major obstacle to achieving postprandial glucose control and, presumably, tighter overall glycemic control. The formulation of remogliflozin proposed provides for a safe, efficacious dosing of an sglt2 inhibitor that can be taken once a day, thus helping to ensure patient compliance.

While it may be difficult to achieve tighter postprandial glucose control in patients with type 2 diabetes, today's new insulin preparations and oral therapies may provide part of the solution to this challenge. Rapid-acting insulin analogs, such as insulin aspen (Novolog) and insulin lispro, produce higher serum insulin levels earlier and have a shorter duration of action than regular human insulin, resulting in lower postprandial glucose excursions with shorter durations of postprandial hyperglycemia, as well as reduced incidence of severe hypoglycemia in patients with type 2 diabetes (18, 19). In this respect, the combination of the formulated remogliflozin etabonate and the aforementioned insulin preparations may provide for a superior control mechanism of postprandial glucose.

While it can be argued that the incidence and severity of hypoglycemia reported in the UKPDS may have been lower if patients had used the new insulin analogs and oral agents in combination with home glucose monitoring technology (which was not widely available when the study started), the risk of hypoglycemia in type 2 diabetes cannot be discounted. All hypoglycemic therapies (secretagogues and insulin) have the potential to cause severe hypoglycemia. Therefore, it is important that health care providers understand the level of risk associated with each therapy utilized and that each therapy be appropriately matched to each patient's ability to recognize and respond to hypoglycemia when it does occur. Remogliflozin showed very little evidence of causing hypoglycemic events, likely due to the mechanism of action.

Large, randomized interventional studies have provided conclusive evidence that achieving and sustaining tight glycemic control (<6.5% A1C) significantly reduces the risk of diabetic microvascular and macrovascular complications. Unfortunately, large epidemiological studies have shown not only that type 2 diabetes is often undermanaged, but also that diabetes in the United States is now an epidemic. Because the greatest increase in prevalence of type 2 diabetes is among adults 30-39 years of age, there will be more people living longer with type 2 diabetes. It is, therefore, imperative that health care providers find ways to improve their effectiveness in treating diabetes in order to prevent years of debilitating complications and an enormous financial burden on the health care system.

To argue that the new glycemic goals are inappropriate because they are unsafe or too difficult to achieve is contrary to sound clinical judgment. The focus should be on achieving the best possible glycemic control for each patient because any reduction in A1C significantly reduces the risk for diabetes complications. Helping patients achieve their best possible level of glycemic control will require the utilization of appropriate therapy, appropriate monitoring, and comprehensive instruction in diabetes self-management.

Citations

1 Marsenic, O. Glucose control by the kidney: an emerging target in diabetes. Am. J. Kidney Dis. 2009, 53, 875-883.
2 Nishimura, M.; Naito, S. Tissue-specific mRNA expression profiles of human ATP-binding cassette and solute carrier transporter superfamilies. Drug Metab. Pharmacokinet. 2005, 20, 452-477.
3 Kanai, Y.; Lee, W. S.; You, G.; Brown, D.; Hediger, M. A. The human kidney low affinity $Na^+$/glucose cotransporter SGLT2: delineation of the major renal reabsorptive mechanism for D-glucose. J. Clin. Invest. 1994, 93, 397-404.
4 Van den Heuvel, L. P.; Assink, K.; Willemsen, M.; Monnens, L. Autosomal recessive renal glucosuria attributable to a mutation in the sodium glucose cotransporter (SGLT2). Hum. Genet. 2002, 111, 544-547.
5 Calado, J.; Soto, K.; Clemente, C.; Correia, P.; Rueff, J. Novel compound heterozygous mutations in SLC5A2 are responsible for autosomal recessive renal glucosuria. Hum. Genet. 2004, 114, 314-316.
6 American Diabetes Association: Postprandial blood glucose (Consensus Statement). Diabetes Care 24:775-778, 2001.
7 Polonsky K S, Given B D, Hirsch U, Tillil H, Shapiro E T, Beebe C, Frank B H, Galloway J A, Van Cauter E: Abnormal patterns of insulin secretion in non-insulin-dependent diabetes mellitus. N Engl J Med 318:1231-1239, 1988.
8 Pfeifer M A, Halter J B, Porte D Jr: Insulin secretion in diabetes mellitus. Am J Med 70:579-88, 1981.
9 Feinglos M N, Thacker C H, English J, Bethel M A, Lane J D: Modification of postprandial hyperglycemia with insulin lispro improves glucose control in patients with type 2 diabetes. Diabetes Care 20:1539-1542, 1997.
10 Bastyr E J, Stuart C A, Brodows R G, Schwartz S, Graf C J, Zagar A, Robertson K E (IOEZ Study Group): Therapy focused on lowering postprandial glucose, not fasting glucose, may be superior for lowering HbA1c. Diabetes Care 23:1236-1241, 2000.
11 De Veciana M, Major C A, Morgan M A, Asrat T, Toohey J S, Lien J M, Evans A T: Postprandial versus preprandial blood glucose monitoring in women with gestational diabetes mellitus requiring insulin therapy. N Engl J Med 333:1239-1241, 1995.
12 American Diabetes Association: Postprandial blood glucose (Consensus Statement). Diabetes Care 24:775-778, 2001.

13 (Stratton I M, Adler A I, Neil H A, Matthews D R, Manley S E, Cull C A, Hadden D, Turner R C, Holman R R: Association of glycaemia with macrovascular and microvascular complications of type 2 diabetes (UKPDS 35): prospective observational study. BMJ 321:405-412, 2000).

14 (Donahue R P, Abbott R D, Reed D M, Yano K: Postchallenge glucose concentration and coronary heart disease in men of Japanese ancestry (Honolulu Heart Program). Diabetes 36:689-692, 1987)

15, (Ziegelasch H J, Lindner J (The DIS Group): Risk factors for myocardial infarction and death in newly detected NIDDM: the Diabetes Intervention Study, 11-year follow-up. Diabetologia 39:1577-1583, 1996)

16, (DECODE Study Group: Glucose tolerance and mortality: comparison of WHO and American Diabetic Association diagnostic criteria. Lancet 354:617-621, 1999)

17. (de Vegt F, Dekker J M, Ruhe H G, Stehouwer C D, Nijpels G, Bouter L M, Heine R J: Hyperglycaemia is associated with all-cause and cardiovascular mortality in the Hoorn population: the Hoorn Study. Diabetologia 42:926-931, 1999)

18 Rosenfalck A M, Thorsby P, Kjems L, Birkeland K, Dejgaard A, Hanssen K F, Madsbad S: Improved postprandial glycaemic control with insulin aspart in type 2 diabetic patients treated with insulin. Acta Diabetol 37:41-46, 2000

19 Anderson J H Jr, Brunelle R L, Keohane P, Koivisto V A, Trautmann M E, Vignati L, DiMarchi R: Mealtime treatment with insulin analog improves postprandial hyperglycemia and hypoglycemia in patients with non-insulin-dependent diabetes mellitus. Multicenter Insulin Lispro Study Group. Arch Intern Med 157:1249-1255, 1997).

20. Moller, D E, New drug targets for type 2 diabetes and the metabolic syndrome, Nature 414, 821-827, 2001.

21. Leth, A, Changes in Plasma and Extracellular Fluid Volumes in Patients with Essential Hypertension During Long-Term Treatment with Hydrochlorothiazide, Circulation 42, 479-485, 1970

22 Rohifing J J, Brunzell J D: The effects of diuretics and adrenergic-blocking agents on plasma lipids. West J. Med. 145:210-218, 1986.

23. Fisher, M. C., Morella, A. M. (1994), European Patent 609961.

24. Hansraj, B. R., Bashir, R. H. (1992), European Patent 502642.

25. Rollet, M. (1987), French Patent 2594693.

26. Howard, S. A., Kotwal, P. M. (1997) U.S. Pat. No. 5,645,858.

27. Macrae, R. J., Smith J. S. (1997), World Patent WO 9718814.

28. Belenduik, G. W., McCarty, J. A., Rudnic, E. M. (1996), U.S. Pat. No. 5,484,608.

29. Bhatti, G. K., Edgren, D. E., Hatamkhani, Z., Wong, P. S., Wong, P. S. L. (1994), World Patent WO 9427589.

30. Palepu, N. R., Venkatesh, G. M., (1997) European Patent 701436.

Remoglifozin Etabonate

Remogliflozin etabonate also known as 5-methyl-4-[4-(1-methylethoxy)benzyl]-1-(1-methylethyl)-1H-pyrazol-3-yl 6-O-(ethoxycarbonyl)-β-D-glucopyranoside of the following formula (I):

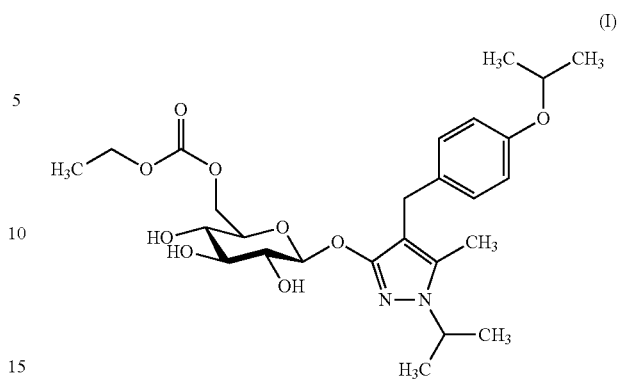

Another nomenclature convention provides this molecule as 3-(6-O-ethoxycarbonyl-.beta.-D-glucopyranosyloxy)-4-[(4-isopropoxyphenyl)methyl]-1-isopropyl-5-methylpyrazole. Remogliflozin etabonate is also known as GSK 189075 or KGT-1681. Salts of compounds of formula (I) are useful as the active ingredient in the pharmaceutical presentation of the invention. Such salts may be as described in U.S. Pat. No. 7,084,123 issued Aug. 1, 2006, herein incorporated by reference. Examples of such salts include acid addition salts with mineral acids such as hydrochloric acid, hydrobromic acid, hydroiodic acid, sulfuric acid, nitric acid, phosphoric acid and the like, acid addition salts with organic acids such as formic acid, acetic acid, methanesulfonic acid, benzenesulfonic acid, p-toluenesulfonic acid, propionic acid, citric acid, succinic acid, tartaric acid, fumaric acid, butyric acid, oxalic acid, malonic acid, maleic acid, lactic acid, malic acid, carbonic acid, glutamic acid, aspartic acid, adipic acid, oleic acid, stearic acid and the like, and salts with inorganic bases such as a sodium salt, a potassium salt, a calcium salt, a magnesium salt and the like.

The compounds represented by the above formula (I) include their solvates with pharmaceutically acceptable solvents such as ethanol and water.

Remogliflozin etabonate may be prepared as described in U.S. Pat. Nos. 7,084,123 and 7,375,087, in particular Example 1 of U.S. Pat. No. 7,084,123, each herein incorporated by reference.

Remogliflozin etabonate is the pro-drug of remogliflozin (also known as GSK189074 or KGT-1650).

Remogliflozin etabonate has the potential to be used as monotherapy for the treatment of T2DM. To date, studies have assessed the efficacy, safety and tolerability up to 12 weeks, with varying efficacy so there is a need to characterize the profile of a number of selected formulated doses over a 12-week period.

The study is designed with a placebo treatment arm to enable the profile of the drug to be further characterized and for maximal glycemic effect to be achieved. However to minimize the time which subjects may have sub-optimal glycemic control, the double blind study medication has been limited to 12 weeks duration. In addition, criteria have been included to allow the introduction of rescue therapy after 6 weeks for those subjects who have a high FP.

Improvements in glycemic control have been achieved in 12 week studies both with once daily (250, 500 and 1000 mg QD) and twice daily (50 mg through 1000 mg BID) dosing. Furthermore, there is evidence that at these doses there may also be clinically relevant weight loss, a key requirement for new T2DM therapies (20). As doses above 250 mg BID may be associated with relatively small incremental benefits on glycemia and weight loss and there is a trend for better tolerability at lower doses, future studies could have total daily doses less than 500 mg per day. Analysis shows that remogliflozin exposures that significantly inhibit the SGLT2 transporter in the sleep period are correlated with small elevations in LDL-c. In particular, the 250 mg and 500 mg bid doses show significant increases in LDL-c. It is believed that the primary mechanism for this isolated increase in LDL-c is due a combination of 1) hemoconcentration as a result of the diuretic effect, similar to that seen with diuretics (21, 22) and 2) SGLT2 overnight inhibition. This is also supported by the higher QD doses exhibiting increases in hematocrit (a surrogate marker for hemoconcentration) but no corresponding increases in LDL-c. Further, a combination IR/SR dose given QD in the morning may also provide meaningful benefits on glycemia and weight loss. From a safety perspective, other than small effects observed on the lipid profile and hematocrit, there was little difference in the safety profile based on the frequency of administration.

Drugs that have absorption limited to the upper gastrointestinal tract coupled with poor absorption in the distal small intestine, large intestine and colon are usually regarded as inappropriate candidates for formulation into oral controlled delivery systems. This limitation on absorption (for example, in the upper gastrointestinal tract) is referred to as the "absorption window".

The gastrointestinal tract functions to propel ingested material from the stomach (where digestion takes place) into the small intestine (where absorption principally occurs) and on to the large intestine (where water is absorbed/secreted as part of body fluid regulation processes). Residence time for non-digestible materials in the stomach depends on whether one is dealing with a fed or a fasted subject. Typical gastric emptying times for particulate material (greater than a few millimeters in diameter) vary from a few tens of minutes in the fasted state to a few hours in the fed state. Transit times through the small intestine are consistently of the order of 3 to 4 hours.

Oral controlled release delivery systems function by releasing their payload of drug over an extended period of time following administration. Thus, controlled release dosage forms may only spend a relatively short period in the regions of the gastrointestinal tract where good absorption of certain drugs can occur. The dosage form will pass on to regions of the intestine where absorption of certain drugs is poor or non-existent, still releasing its contained drug albeit with a significant percentage of its payload still to be delivered. Drug when released from the dosage form in the circumstances described will not be absorbed. Thus, administration of a drug subject to a window of absorption in a conventional controlled release delivery system can lead to subtherapeutic blood levels and ineffective treatment of the disease state for which the drug was intended.

In a controlled release dosage form, the formulator tries to reduce the rate of dissolution by, for example, embedding the drug in a polymeric matrix or surrounding it with a polymeric barrier membrane through which drug must diffuse to be released for absorption. To reduce the rate of release of drug from the dosage form to an appropriate level consistent with the blood level profile desired for a drug possessing very high water solubility, very large amounts of polymer would be required for the matrix or barrier membrane. If the total daily dose of drug to be delivered is of the order of only a few milligrams this may be feasible, but many drugs having the solubility properties described require total daily doses of the order of many hundreds of milligrams. Whilst it is possible to create oral controlled release dosage forms for such products by use of large amounts of polymer, an unacceptably large dosage form may result.

Improvements in the therapeutic regimes employing remogliflozin etabonate may be achieved by a dosage form that allows a reduction in dosing frequency, i.e., once daily versus twice daily, providing patient convenience that would probably improve compliance. Conventional modified release formulations have been demonstrated to not compensate for the short half-life inherent in this molecule, thus indicating the only way to deliver remogliflozin etabonate is by twice daily dosing. To reduce dosing frequency, the type of release from the dosage form should be such as to extend effective plasma levels, but the potential for effective delivery at this rate is compromised by the combined influences of the significant reduction in permeability to the drug in passing from the proximal small intestine down to the colon and the limited residence time in the regions of the gastrointestinal tract where the drug is well absorbed. That transit time down the "useful" region of the gastrointestinal tract is only likely to be of the order of a few hours. Maintained or even improved bioavailability from a dosage form that releases remogliflozin etabonate in a combination manner provides the desired plasma levels of drug for the time period desired which is typically the waking hours of the patient.

Formulations

Typical prior art techniques for creating a controlled release oral dosage form would involve either matrix systems or multi particulate systems. Matrix systems may be formulated by homogeneously mixing drug with hydrophilic polymers, such as hydroxypropylmethylcellulose, hydroxypropylcellulose, polyethylene oxide, carbomer, certain methacrylic acid derived polymers, sodium alginate, or mixtures of components selected from these, and compressing the resultant mixture into tablets (employing some other excipients where needed). Hydrophobic polymers, such as ethyl cellulose, certain polymeric methacrylic acid esters, cellulose acetate butyrate, poly (ethylene-co-vinyl-acetate) may be uniformly incorporated with the above materials to give additional control of release. A further alternative involves embedding drug within a wax based tablet, by granulation or simply mixing of drug with a wax, such as carnauba wax, microcrystalline wax or commercially available purified fatty acid esters. As noted above, it may not be possible to use these approaches with very highly water soluble drugs.

Multi particulate systems consist of a dosage form based on a plurality of drug loaded spheres, prepared by layering drug onto a core, usually a sugar-starch mixture sphere of around 0.8 mm diameter, until a sufficient level is reached, and then providing a drug release barrier around the drug-loaded sphere. Drug-loaded spheres can also be made by wet massing a mixture of drug and excipients, forcing the wet mass through a perforated screen to form short strands which are rounded in a spheronization apparatus before drying and having the drug release barrier applied. The drug release barrier can be a wax, such as carnauba wax or glyceryl fatty acid esters, or a polymeric barrier, such as a mixture of ethyl cellulose and hydroxypropylmethylcellulose. These work well for moderately soluble drugs with doses in the units of milligrams to less than a few hundred milligrams per day.

In several examples, systems seem to provide a controlled release formulation of a very water soluble drug by improving the multi particulate system approach. Fisher discloses a multi particulate system for highly soluble drugs especially opiate agonists (23) based on drug containing cores surrounded by a drug release controlling barrier which has the property of being partially soluble at a highly acidic pH.

Hansraj (24) coats drug loaded cores with methacrylic or acrylic acid derived polymers whose properties are modified by inclusion of at least one anionic surfactant. In such a system, drug release of highly water soluble drugs is controlled without having to resort to the use of thick coatings on the release rate controlling layer.

Rollet (25) achieves prolonged release of a drug from a multi particulate formulation based on fine particles of hydrophilic and hydrophobic silicas or silicates. Presumably, this system would function for drugs of high water solubility.

Multi particulate systems are usually filled into capsules to provide unit dose forms because of the damage caused to such particles in trying to compress them into tablets. Total dose contained in a single unit is constrained by the loading possible in a hard gelatin capsule of easily swallowable size and is usually not more than a few hundred milligrams.

Single unit controlled release systems applicable to highly water soluble drugs include the application of multiple layers around a dose form as described by Howard (26). Where coating is not employed, special mixtures of polymers or formation of a complex with the drug have been used. Macrae (27) uses mixtures of polyethylene oxide and hydroxypropylmethylcellulose with optional enteric polymers to produce a constant release rate for highly water soluble drugs. Belenduik (28) combines the highly water soluble drug with a hydrophilic polymer based on acrylic acid and disperses this in a hydrophobic matrix. Variations of ALZA osmotic systems have been described suitable for highly water soluble drugs such as venlafaxine hydrochloride (29). These systems need two layers, a drug layer and an osmotically driven displacement layer all surrounded by water permeable/drug impermeable membrane with an exit passage in this membrane for the drug.

Granules of highly water soluble clavulanate were prepared (30) having to employ a barrier layer of a hydrophobic waxy material in order to provide for controlled release of this material when co-formulated with controlled release amoxycillin trihydrate granules in capsule or compressed tablet.

DETAILED DESCRIPTION OF THE INVENTION

The present invention comprises formulating a drug with a relatively short half life and a limited window of absorption such as remogliflozin etabonate or a salt thereof which has a window of absorption in the upper gastrointestinal tract, to provide a dosage form that can provide effective exposures during the patient's waking hours. The formulation of the invention (a) provides immediate release of the drug, typically before or at breakfast, and (b) a delayed release adequately to provide sufficient coverage for glucose excursions later in the day. The formulations of the invention will provide for an immediate/delayed release formulation of drug.

In the case of remogliflozin etabonate, the formulation of the invention allows a patient a dosing regimen of at least 250 mg remogliflozin etabonate, once-daily, to 500 mg remogliflozin etabonate, once daily, in the form of one solid dosage form such as a tablet or one capsule, while providing effective control of plasma glucose. The remogliflozin etabonate formulations of the invention may be administered once daily at the above dosages to effectively treat diabetes while avoiding problems which may be associated with high night time plasma remogliflozin etabonate levels as may be encountered with twice daily dosing of remogliflozin etabonate, while providing optimum therapeutic control and optimal safety profile.

The invention is applicable to all drugs having short half-lives and a limited window of absorption in the treatment of diabetes and in particular, where the mechanism of action involves attenuating or blunting prandial glucose excursions.

The combination immediate release delivery system of the invention is a heterogeneous two phase system which includes (1) a solid particulate phase in the form of individual granules or particles containing (a) drug which has a short half life, preferably, remogliflozin etabonate or a salt thereof, and a limited window of absorption (such as in the upper gastrointestinal tract), and (b) a delayed release material formed of one or more hydrophilic polymers, and/or one or more hydrophobic polymers, and/or one or more other type hydrophobic materials (such as one or more waxes, fatty alcohols and/or fatty acid esters), and (2) a solid phase in which granules or particles of the delayed release solid particulate phase are dispersed and embedded, the solid phase which primarily is formed of an immediate release material formed of one or more hydrophilic polymers, and/or one or more hydrophobic polymers, and/or one or more other type hydrophobic materials (such as one or more waxes, fatty alcohols and/or fatty acid esters).

The invention is particularly adapted for delivery of short half-life drugs, such as remogliflozin etabonate and pharmaceutically acceptable salts thereof, in a controlled manner with a significant initial burst of drug, and subsequent delayed release of drug (liberated from the individual dispersed particles forming a solid particulate phase) at some time relevant to the absorption window in the upper GI tract. Drug upon being released from the particles of the delayed release formulation, in effect, becomes into the upper gastrointestinal tract to be available for absorption.

The solid phase immediate release formulation is particularly a phase or matrix having the particles or granules including drug (forming the delayed release solid phase) dispersed throughout and embedded in the solid phase immediate release formulation.

In addition, in accordance with the present invention, a method for lowering insulin resistance or treating diabetes is provided wherein the combination immediate/delayed release formulation of the invention containing an antidiabetic pharmaceutical is administered to a patient in need of treatment.

The term "diabetes" as employed herein refers to type 2 diabetes and type 1 diabetes, usually type 2 diabetes.

The antidiabetic pharmaceutical employed is particularly an SGLT2 inhibitor, such as remogliflozin etabonate or a pharmaceutically acceptable salt thereof such as the hydrochloride, all of which are collectively referred to as remogliflozin etabonate. Remogliflozin etabonate hydrochloride salt is a particular active ingredient for the invention. In another aspect of the present invention, a method is provided for lowering insulin resistance or treating diabetes wherein the combination immediate/delayed release formulation of the invention contains remogliflozin etabonate and is administered in a dosing regimen of at least about 250 mg remogliflozin etabonate, once daily, particularly from about 250 mg to 500 mg, once daily, to a patient in need of treatment.

The term "release material" as present in the solid particulate phase delayed release formulation and the solid phase immediate release formulation refers to one or more hydrophilic polymers and/or one or more hydrophobic polymers and/or one or more other type hydrophobic materials, such as, for example, one or more waxes, fatty alcohols and/or fatty acid esters. The "release material" present in the delayed release particulate phase may be the same as or different from the "release material" present in the immediate release solid phase, although different grades or molecular weights of the same chemical polymer may be used. However, it is typical that the "release material" present in the delayed release particulate phase may be different from the "release material in the immediate release formulation.

The term "limited window of absorption" or similar term when characterizing a drug, medicament or pharmaceutical for use in the formulation of the invention refers to an oral bioavailability of less than about 75%, usually less than about 60%, usually decreasing with increasing dose, and almost invariably having permeability/transit time limited absorption.

The combination immediate/delayed release system of the invention may include the delayed release solid particulate phase in a weight ratio to the immediate release solid phase within the range from about 0.5:1 to about 4:1, such as from about 0.8:1 to about 2:1.

The delayed release solid particulate phase will contain drug in an amount within the range from about 10 to about 98% by weight, such as from about 15 to about 95% by weight, and extended release material in the form of hydrophilic polymers and/or hydrophobic polymers and/or other hydrophobic material in an amount within the range from about 5 to about 95% by weight, particularly from about 7 to about 85% by weight, the above % being based on the weight of the delayed release solid particulate phase. Where mixtures are employed, the hydrophilic polymer will be employed in a weight ratio to hydrophobic polymer and/or other hydrophobic material within the range from about 0.05:1 to about 19:1, particularly from about 0.1:1 to about 10:1.

The particles or granules of the delayed release solid particulate phase will have a mean particle size within the range from about 30 µm to about 0.8 mm, and particularly from about 50 µm to about 0.5 mm.

The immediate release solid phase will contain immediate release material (normally different from that employed in the delayed release solid particulate phase) in the form of one or more hydrophilic polymers and/or hydrophobic polymers and/or other hydrophobic material in an amount within the range from about 40 to about 100%, particularly from about 60 to about 100% (based on the weight of the immediate release solid phase).

The pharmaceutical formulation of the invention will have a total polymer extended release material content (including hydrophilic polymers and/or hydrophobic polymers and/or other hydrophobic material present in the delayed release solid particulate phase and hydrophilic polymer and/or hydrophobic polymers and/or other hydrophobic material present in the immediate release solid phase) within the range from about 25 to about 75% by weight, particularly from about 30 to about 65%, more particularly from about 35 to about 60% by weight based on the total weight of the pharmaceutical formulation.

Hydrophilic polymers which may be employed in the delayed release solid particulate phase and/or immediate release solid phase include, but are not limited to hydroxypropylmethylcellulose, hydroxypropylcellulose, sodium carboxymethylcellulose, carboxymethylcellulose calcium, ammonium alginate, sodium alginate, potassium alginate, calcium alginate, propylene glycol alginate, alginic acid, polyvinyl alcohol, povidone, carbomer, potassium pectate, potassium pectinate, and the like.

Hydrophobic polymers which may be employed in the delayed release solid particulate phase and/or immediate release solid phase include, but are not limited to ethyl cellulose, hydroxyethylcellulose, ammonio methacrylate copolymer (Eudragit R L™ or Eudragit RS™), methacrylic acid copolymers (Eudragit L™ or Eudragit S™), methacrylic acid-acrylic acid ethyl ester copolymer (Eudragit L 100-5™), methacrylic acid esters neutral copolymer (Eudragit NE 30D™), dimethylaminoethylmethacrylate-methacrylic acid esters copolymer (Eudragit E 100™), vinyl methyl ether/maleic anhydride copolymers, their salts and esters (Gantrez™).

Other hydrophobic materials which may be employed in the delayed release solid particulate phase and/or immediate release solid phase include, but are not limited to waxes such as beeswax, carnauba wax, microcrystalline wax, and ozokerite; fatty alcohols such as cetostearyl alcohol, stearyl alcohol; cetyl alcohol and myristyl alcohol; and fatty acid esters such as glyceryl monostearate, glycerol monooleate, acetylated monoglycerides, tristearin, tripalmitin, cetyl esters wax, glyceryl palmitostearate, glyceryl behenate, and hydrogenated castor oil.

Where hydrophilic polymers and/or hydrophobic polymers are used in the delayed release solid particulate phase and/or the immediate release solid phase, such polymers can be ionic or non-ionic, particularly ionic for the delayed release solid particulate phase and particularly non-ionic for the immediate release solid phase.

Particular ionic polymers for use in the delayed release solid particulate phase include sodium alginate, carbomer (Carbopol™), calcium carboxymethylcellulose, or sodium carboxymethylcellulose, xanthan gum, methacrylic acid-acrylic acid ethyl ester copolymer, dimethylaminoethyl-methacrylate-methacrylic acid esters copolymer, cellulose acetate phthalate, hydroxypropyl-methylcellulose phthalate, hydroxypropylmethylcellulose trimellitate, and hydroxypropylmethylcellulose maleate, with sodium carboxymethylcellulose being particular. Particular biphasic immediate/delayed release delivery systems in accordance with the present invention are as set forth in the Examples A particular active ingredient is the remogliflozin etabonate hydrochloride salt.

Combinations

Where desired, remogliflozin etabonate or a salt thereof may be used in combination with another antihyperglycemic agent and/or a hypolipidemic agent and/or antiobesity agent which may be administered orally in the same dosage form in accordance with the invention, a separate oral dosage form or by injection. The remogliflozin etabonate or salt thereof will be employed in a weight ratio to the other antihyperglycemic agent and/or hypolipidemic agent and/or antiobesity agent within the range from about 0.01:1 to about 300:1, particularly from about 0.05:1 to about 250:1.

The use of the remogliflozin etabonate or salt thereof in combination with another anti-hyperglycemic agent may be of particular use in achieving antihyperglycemic results compared to each of these medicaments alone and greater than the combined additive anti-hyperglycemic effects produced by these medicaments.

In addition, in accordance with the present invention a method is provided for lowering insulin resistance or treating hyperglycemia including type 2 diabetes (NIDDM) and/or type 1 diabetes (IDDM) wherein a therapeutically effective amount of the combination formulation of the invention containing remogliflozin etabonate or a salt thereof, optionally in combination with another antihyperglycemic agent and/or a hypolipidemic agent and/or an anti-obesity agent, is administered to a patient in need of treatment.

The other antihyperglycemic agent may be an oral antihyperglycemic agent particularly a biguanide such as metformin (commonly sold as Glucophage) or other known biguanides that improve hyperglycemia primarily through suppression of hepatic glucose production The other antihyperglycemic agent may be an oral antihyperglycemic agent particularly a sulfonyl urea such as glyburide (also known as glibenclamide), glimepiride (disclosed in U.S. Pat. No. 4,379,785), glipizide, gliclazide or chlorpropamide, other known sulfonylureas or other antihyperglycemic agents which act on the ATP-dependent channel of the β-cells.

The remogliflozin etabonate or salt thereof will be employed in a weight ratio to the sulfonyl urea in the range from about 300:1 to about 50:1, particularly from about 250:1 to about 75:1.

The oral antihyperglycemic agent may also be a glucosidase inhibitor such as acarbose (disclosed in U.S. Pat. No. 4,904,769) or miglitol (disclosed in U.S. Pat. No. 4,639,436), which may be administered in a separate oral dosage form.

The remogliflozin etabonate salt thereof will be employed in a weight ratio to the glucosidase inhibitor within the range from about 300:1 to about 2:1, such as from about 200:1 to about 25:1.

The remogliflozin etabonate or salt thereof may be employed in combination with a thiazolidinedione oral anti-diabetic agent (which has an insulin sensitivity effect in NIDDM patients) such as troglitazone (Warner-Lambert's Rezulin®, disclosed in U.S. Pat. No. 4,572,912), rosiglitazone (SKB), pioglitazone (Takeda), Mitsubishi's MCC-555 (disclosed in U.S. Pat. No. 5,594,016) Glaxo-Welcome's GL-262570, englitazone (CP-68722, Pfizer) or darglitazone (CP-86325, Pfizer).

The remogliflozin etabonate or salt thereof will be employed in a weight ratio to the thiazolidinedione in an amount within the range from about 75:1 to about 0.1:1, such as from about 5:1 to about 0.5:1.

The sulfonyl urea and thiazolidinedione in amounts of less than about 150 mg oral anti-diabetic agent may be incorporated in a single tablet with the formulation of the invention as a separate rapidly dissolving layer.

The remogliflozin etabonate or salt thereof may also be employed in combination with a non-oral antihyperglycemic agent such as insulin or with glucagon-like peptide-1 (GLP-1) such as GLP-1 (1-36) amide, GLP-1 (7-36) amide, GLP-1 (7-37) (as disclosed in U.S. Pat. No. 5,614,492 to Habener, the disclosure of which is incorporated herein by reference), which may be administered via injection, or by transdermal or buccal devices.

The oral antihyperglycemic agent may also be a dipeptidyl protease IV (DPP-IV) inhibitor such as sitigliptin, vildagliptin, saxagliptin, linagliptin (being developed by Boehringer Ingelheim), or alogliptin.

Where present, the sulfonyl ureas, such as glyburide, glimepiride, glipyride, glipizide, glipizide, chlorpropamide and gliclazide and the glucosidase inhibitors acarbose or miglitol may be employed in formulations as described above and in amounts and dosing as indicated in the Physician's Desk Reference.

Where present, the thiazolidinedione anti-diabetic agent may be employed in amounts within the range from about 0.01 to about 2000 mg/day which may be administered in single or divided doses one to four times per day.

Where present insulin may be employed in formulations, amounts and dosing as indicated by the Physician's Desk Reference.

Where present GLP-1 peptides may be administered in oral buccal formulations, by nasal administration or parenterally as described in U.S. Pat. No. 5,346,701 (TheraTech), U.S. Pat. Nos. 5,614,492 and 5,631,224 which are incorporated herein by reference.

The use of the remogliflozin etabonate or salt thereof in combination with another particular anti-hyperglycemic agent may produce antihyperglycemic results greater than that possible from each of these medicaments alone and greater than the combined additive anti-hyperglycemic effects produced by these medicaments.

In addition, in accordance with the present invention a method is provided for lowering insulin resistance or treating hyperglycemia including type 2 diabetes (NIDDM) and/or type 1 diabetes (IDDM) wherein a therapeutically effective amount of the formulation of the invention containing remogliflozin etabonate or a salt thereof, optionally in combination with an antiobesity agent, is administered to a patient in need of treatment.

In addition, in accordance with the present invention a method is provided for effecting weight loss wherein a therapeutically effective amount of the formulation of the invention containing remogliflozin etabonate or a salt thereof, optionally in combination with an antiobesity agent, is administered to a patient in need of treatment.

The antiobesity agent may be an oral antiobesity agent, particularly a pancreatic lipase inhibitor, an anorectic, a cannabinoid receptor (CB-1) antagonist, a 5HTC agonist, or a dopamine receptor antagonist, with examples being xenical, sibutramine, phentermine, fenfluramine, rimonabant, lorcaserin, or bupropion.

The antiobesity agent may be an oral antiobesity agent particularly a pancreatic lipase inhibitor such as xenical (Orlistat/Alli).

The remogliflozin etabonate or salt thereof will be employed in a weight ratio to the obesity agent in the range from about 300:1 to about 50:1, such as from about 250:1 to about 75:1

The oral antiobesity agent may also be an anorectic such as phentermine, fenfluramine, or lorcaserin The remogliflozin etabonate salt thereof will be employed in a weight ratio to the anorectic within the range from about 300:1 to about 2:1, such as from about 200:1 to about 25:1.

The remogliflozin etabonate or salt thereof may be employed in combination with an oral antiobesity agent such as a cannabinoid-1 receptor antagonist The remogliflozin etabonate or salt thereof will be employed in a weight ratio to the cannabinoid-1 receptor antagonist in an amount within the range from about 75:1 to about 0.1:1, such as from about 5:1 to about 0.5:1.

The remogliflozin etabonate or salt thereof may also be employed in combination with a non-oral antiobesity agent such as leptin, which may be administered via injection, or by transdermal or buccal devices.

The hypolipidemic agent which may be optionally employed in combination with remogliflozin etabonate or a salt thereof may include MTP inhibitors, HMG CoA reductase inhibitors, squalene synthetase inhibitors, fibric acid derivatives, ACAT inhibitors, cholesterol absorption inhibitors, ileal Na.sup.+/bile acid cotransporter inhibitors, bile acid sequestrants, and/or nicotinic acid and derivatives thereof.

MTP inhibitors employed herein include MTP inhibitors disclosed in U.S. Pat. Nos. 5,595,872, 5,739,135, 5,712,279, 5,760,246, 5,827,875, 5,885,983 and U.S. application Ser. No. 09/175,180 filed Oct. 20, 1998, now U.S. Pat. No. 5,563,440.

Particular MTP inhibitors to be employed in accordance with the present invention include MTP inhibitors as set out in U.S. Pat. Nos. 5,739,135 and 5,712,279, and U.S. Pat. No. 5,760,246.

The hypolipidemic agent may be an HMG CoA reductase inhibitor which includes, but is not limited to, mevastatin and related compounds as disclosed in U.S. Pat. No. 3,983, 140, lovastatin (mevinolin) and related compounds as disclosed in U.S. Pat. No. 4,231,938, pravastatin and related compounds such as disclosed in U.S. Pat. No. 4,346,227, simvastatin and related compounds as disclosed in U.S. Pat. Nos. 4,448,784 and 4,450,171. Other HMG CoA reductase inhibitors which may be employed herein include, but are not limited to, fluvastatin, disclosed in U.S. Pat. No. 5,354, 772, cerivastatin disclosed in U.S. Pat. Nos. 5,006,530 and 5,177,080, atorvastatin disclosed in U.S. Pat. Nos. 4,681, 893, 5,273,995, 5,385,929 and 5,686,104, pyrazole analogs of mevalonolactone derivatives as disclosed in U.S. Pat. No. 4,613,610, indene analogs of mevalonolactone derivatives as disclosed in PCT application WO 86/03488, 6-[2-(substituted-pyrrol-1-yl)-alkyl)pyran-2-ones and derivatives thereof as disclosed in U.S. Pat. No. 4,647,576, Searle's SC-45355 (a 3-substituted pentanedioic acid derivative) dichloroacetate, imidazole analogs of mevalonolactone as disclosed in PCT application WO 86/07054, 3-carboxy-2-hydroxy-propane-phosphonic acid derivatives as disclosed in French Patent No. 2,596,393, 2,3-disubstituted pyrrole, furan and thiophene derivatives as disclosed in European Patent Application No. 0221025, naphthyl analogs of mevalonolactone as disclosed in U.S. Pat. No. 4,686,237, octahydronaphthalenes such as disclosed in U.S. Pat. No. 4,499, 289, keto analogs of mevinolin (lovastatin) as disclosed in European Patent Application No. 142,146 A2, as well as other known HMG CoA reductase inhibitors.

In addition, phosphinic acid compounds useful in inhibiting HMG CoA reductase suitable for use herein are disclosed in GB 2205837.

The squalene synthetase inhibitors suitable for use herein include, but are not limited to, .alpha.-phosphono-sulfonates disclosed in U.S. Pat. No. 5,712,396, those disclosed by Biller at al, J. Med. Chem., 1988, Vol. 31, No. 10, pp 1869-1871, including isoprenoid (phosphinylmethyl)phosphonates as well as other squalene synthetase inhibitors as disclosed in U.S. Pat. Nos. 4,871,721 and 4,924,024 and in Biller, S. A., Neuenschwander, K., Ponpipom, M. M., and Poulter, C. D., Current Pharmaceutical Design, 2, 1-40 (1996).

In addition, other squalene synthetase inhibitors suitable for use herein include the terpenoid pyrophosphates disclosed by P. Ortiz de Montellano et al, J. Med. Chem., 1977, 20, 243-249, the farnesyl diphosphate analog A and presqualene pyrophosphate (PSQ-PP) analogs as disclosed by Corey and Volante, J. Am. Chem. Soc., 1976, 98, 1291-1293, phosphinyiphosphonates reported by McClard, R. W. et al, J. A. C. S., 1987, 109, 5544 and cyclopropanes reported by Capson, T. L., PhD dissertation, June, 1987, Dept. Med. Chem. U of Utah, Abstract, Table of Contents, pp 16, 17, 40-43, 48-51, Summary.

Other hypolipidemic agents suitable for use herein include, but are not limited to, fibric acid derivatives, such as fenofibrate, gemfibrozil, clofibrate, bezafibrate, ciprofibrate, clinofibrate and the like, probucol, and related compounds as disclosed in U.S. Pat. No. 3,674,836, probucol and gemfibrozil being examples, bile acid sequestrants such as cholestyramine, colestipol and DEAE-Sephadex (Secholex®, Policexide®), as well as lipostabil (Rhone-Poulenc), Eisai E-5050 (an N-substituted ethanolamine derivative), imanixil (HOE-402), tetrahydrolipstatin (THL), istigmastanyiphosphorylcholine (SPC, Roche), aminocyciodextrin (Tanabe Seiyoku), Ajinomoto AJ-814 (azulene derivative), melinamide (Sumitomo), Sandoz 58-035, American Cyanamid CL-277,082 and CL-283,546 (disubstituted urea derivatives), nicotinic acid, acipimox, acifran, neomycin, p-aminosalicylic acid, aspirin, poly(diallylmethylamine) derivatives such as disclosed in U.S. Pat. No. 4,759,923, quaternary amine poly(diallyldimethylammonium chloride) and ionenes such as disclosed in U.S. Pat. No. 4,027,009, and other known serum cholesterol lowering agents.

The hypolipidemic agent may be an ACAT inhibitor such as disclosed in, "The ACAT inhibitor, Cl-1011 is effective in the prevention and regression of aortic fatty streak area in hamsters", Nicolosi et al, Atherosclerosis (Shannon, Irel). (1998), 137(1), 77-85; "The pharmacological profile of FCE 27677: a novel ACAT inhibitor with potent hypolipidemic activity mediated by selective suppression of the hepatic secretion of ApoB100-containing lipoprotein", Ghiselli, Giancarlo, Cardiovasc. Drug Rev. (1998), 16(1), 16-30; "RP 73163: a bioavailable alkylsulfinyl-diphenylimidazole ACAT inhibitor", Smith, C., et al, Bioorg. Med. Chem. Lett. (1996), 6(1), 47-50; "ACAT inhibitors: physiologic mechanisms for hypolipidemic and anti-atherosclerotic activities in experimental animals", Krause et al, Editor(s): Ruffolo, Robert R., Jr.; Hollinger, Mannfred A., Inflammation: Mediators Pathways (1995), 173-98, Publisher: CRC, Boca Raton, Fla.; "ACAT inhibitors: potential anti-atherosclerotic agents", Sliskovic et al, Curr. Med. Chem. (1994), 1(3), 204-25; "Inhibitors of acyl-CoA:cholesterol O-acyl transferase (ACAT) as hypocholesterolemic agents. 6. The first water-soluble ACAT inhibitor with lipid-regulating activity. Inhibitors of acyl-CoA:cholesterol acyltransferase (ACAT). 7. Development of a series of substituted N-phenyl-N'-[(1-phenylcyclopentyl)methyl]ureas with enhanced hypocholesterolemic activity", Stout et al, Chemtracts: Org. Chem. (1995), 8(6), 359-62.

The cholesterol absorption inhibitor may be Schering-Plough's SCH 48461 or as disclosed in Atherosclerosis 115, 45-63 (1995) or J. Med. Chem. 41, 973 (1998).

The ileal Na.sup.+/bile acid cotransporter inhibitor may be as disclosed in Drugs of the Future, 24, 425-430 (1999). Particular hypolipidemic agents are pravastatin, lovastatin, simvastatin, atorvastatin, fluvastatin and cerivastatin.

The above-mentioned U.S. patents are incorporated herein by reference. The amounts and dosages employed will be as indicated in the Physician's Desk Reference and/or in the patents set out above.

The compounds of formula (I) of the invention will be employed in a weight ratio to the hypolipidemic agent (where present), within the range from about 500:1 to about 1:500, particularly from about 100:1 to about 1:100.

The dose administered must be carefully adjusted according to age, weight and condition of the patient, as well as the route of administration, dosage form and regimen and the desired result.

The dosages and formulations for the hypolipidemic agent will be as disclosed in the various patents, papers and applications discussed above.

The dosages and formulations for the other hypolipidemic agent to be employed, where applicable, will be as set out in the latest edition of the Physicians' Desk Reference.

For oral administration, a satisfactory result may be obtained employing the MTP inhibitor in an amount within the range of from about 0.01 mg/kg to about 100 mg/kg, such as from about 0.1 mg/kg to about 75 mg/kg, one to four times daily.

A particular oral dosage form, such as tablets or capsules, will contain the MTP inhibitor in an amount of from about 1 to about 500 mg, particularly from about 2 to about 400 mg, such as from about 5 to about 250 mg, one to four times daily.

For parenteral administration, the MTP inhibitor will be employed in an amount within the range of from about 0.005 mg/kg of body weight to about 10 mg/kg and particularly from about 0.005 mg/kg to about 8 mg/kg, one to four times daily.

For oral administration, a satisfactory result may be obtained employing an HMG CoA reductase inhibitor, for example, pravastatin, lovastatin, simvastatin, atorvastatin, fluvastatin or cerivastatin in dosages employed as indicated in the Physician's Desk Reference, such as in an amount within the range of from about 1 to 2000 mg, and particularly from about 4 to about 200 mg.

The squalene synthetase inhibitor may be employed in dosages in an amount within the range of from about 10 mg to about 2000 mg and particularly from about 25 mg to about 200 mg.

A particular oral dosage form, such as tablets or capsules, will contain the HMG CoA reductase inhibitor in an amount from about 0.1 to about 100 mg, such as from about 5 to about 80 mg, and more particularly from about 10 to about 40 mg.

A particular oral dosage form, such as tablets or capsules will contain the squalene synthetase inhibitor in an amount of from about 10 to about 500 mg, particularly from about 25 to about 200 mg.

The remogliflozin etabonate or salt thereof and the hypolipidemic agent may be employed together in the same oral dosage form or in separate oral dosage forms taken at the same time.

The compositions described above may be administered in the dosage forms as described above in single or divided doses, once daily and up to four times daily. It may be advisable to start a patient on a low dose combination and work up gradually to a high dose combination.

Particular hypolipidemic agents are pravastatin, simvastatin, lovastatin, atorvastatin, fluvastatin or cerivastatin.

The following additional type high water soluble drugs may be employed in the delivery system of the invention: pravastatin; antihypertensives and antidepressants related to guanethidine (as disclosed in U.S. Pat. No. 2,928,829) and related to guanoxyfen (as disclosed in BE612362); antibiotics and viricides such as related to amidinomycin (as disclosed in JP 21,418); stallimycin (as disclosed in DE 1,039,198); Arphamenine B (as disclosed in published European Patent Application 85/133550A2); chitinovorin-A (as disclosed in published European Patent Application 85/150, 378A2 and U.S. Pat. No. 4,723,004); streptomycin (as disclosed in U.S. Pat. No. 2,868,779); SB-59 (as disclosed in Justus Liebigs, Ann. Chem. (1973) 7, 1112-1140); TAN-1057-A (as disclosed in U.S. Pat. No. 4,971,965); streptoniazid (as disclosed in J. Am. Chem. Soc. (1953) 75, 2261); immunostimulants related to ST-789 (as disclosed in published European Patent Application 88/260588); peptide hydrolase inhibitors related to nafamastat (as disclosed in U.S. Pat. No. 4,454,338); gabexate (as disclosed in U.S. Pat. No. 3,751,447); sepimostat (as disclosed in U.S. Pat. Nos. 4,777,182 and 4,820,730); Factor Xa inhibitors related to DX-9065a (as disclosed in published European Patent Application 92/0540051); anti-inflammatory agents related to paranyline as disclosed in U.S. Pat. No. 2,877,269; peptidyl aldehydes (as disclosed in WO94/13693); antianaphylactics related to GMCHA-TBP (Batebulast) (as disclosed in U.S. Pat. No. 4,465,851); anti-ulcer agents related to benexate (as disclosed in U.S. Pat. No. 4,348,410); deoxyspergualin (as disclosed in U.S. Pat. Nos. 4,518,532, 4,658,058 and 4,983,328); and arginine.

Other water-soluble drugs suitable for use herein include peptides having a molecular weight from about 100 to 10,000, more particularly from about 100 to about 6,000 and having from 2 to 35 amino acid moieties. Higher molecular weight peptides, even those with a molecular weight of above 10,000, up to about 50,000, may also be accommodated in formulations of the present invention.

Suitable small peptides have from about 2 to about 10, more particularly from about 2 to about 6 amino acid moieties. Small peptides include the fibrinogen receptor antagonists (RGD containing peptides) which are tetrapeptides with an average molecular weight of about 600. These peptide antagonists are highly potent platelet aggregation inhibitors at plasma levels as low as 1 pmol/mL. Particular fibrinogen antagonists include the peptide cyclo(S,S)-Na-acetyl-Cys-(N$^a$-methyl)Arg-Gly-Asp-Pen-NH$_2$ (Ali et al, EP 0341915, whose disclosure is herein incorporated by reference) and the peptide cyclo(S,S)-(2-mercapto) benzoyl-(N$^a$-methyl)Arg-Gly-Asp-(2-mercapto)-phenylamide (EP 0423212, whose disclosure is herein incorporated by reference). Other fibrinogen antagonists useful in the present invention are those peptides disclosed by Pierschbacher et al, WO 89/05150 (U.S. Pat. No. 8,804, 403); Marguerie, EP 0275748; Adams et al, U.S. Pat. No. 4,857,508; Zimmerman et al, U.S. Pat. No. 4,683,291; Nutt et al, EP 0410537, EP 0410539, EP 0410540, EP 0410541, EP 0410767, EP 0410833, EP 0422937 and EP 0422938; Ali et al, EP 0372486; Ohba et al, WO 90/02751 (PCT/JP89/00926); Klein et al, U.S. Pat. No. 4,952,562; Scarborough et al, WO 90/15620 (PCT/US90/03417); Ali et al, PC/US90/06514 and PCT/US92/00999; the peptide-like compounds disclosed by All et al, EP 0381033 and EP 0384362; and the RGD peptide cyclo-N$^a$-acetyl-Cys-Asn-Dtc-Amf-Gly-Asp-Cys-OH (in which Dtc is 4,4'-dimethylthia-zolidine-5-carboxylic acid and Amf is 4-aminomethylphenyl-alanine).

The RGD peptide may be usefully included in the formulation of the invention in an amount up to about 600 mg/g of the hydrophilic phase or from 0.1 to 60 mg/g of the formulation.

Other peptides useful in the present invention include, but are not limited to, other RGD containing peptides such as those disclosed by Momany, U.S. Pat. Nos. 4,411,890 and 4,410,513; Bowers et al, U.S. Pat. Nos. 4,880,778, 4,880, 777, 4,839,344; and WO 89/10933 (PCT/US89/01829); the peptide Ala-His-D-NaI-Ala-Trp-D-Phe-Lys-NH$_2$ (in which NaI represents b-naphthyl-alanine) and the peptides disclosed by Momany, U.S. Pat. Nos. 4,228,158, 4,228,157, 4,228,156, 4,228,155, 4,226,857, 4,224,316, 4,223,021, 4,223,020, 4,223,019 and 4,410,512.

Other suitable peptides include hexapeptides such as the growth hormone releasing peptide (GHRP) His-D-Trp-Ala-Trp-D-Phe-Lys-NH.sub.2, (Momany, U.S. Pat. No. 4,411,890, the disclosure of which is herein incorporated by reference in its entirety). This may usefully be included in an amount up to about 250 mg/g of the hydrophilic phase or from 0.1 to 25 mg/kg of the formulation.

Suitable larger polypeptides and proteins for use in the controlled release formulations of the present invention include insulin, calcitonin, elcatonin, calcitoningene related peptide and porcine somatostatin as well as analogs and homologs thereof. Other suitable larger polypeptides include those disclosed by Pierschbacher et al, U.S. Pat. No. 4,589,881 (>30 residues); Bittle et al, U.S. Pat. No. 4,544,500 (20-30 residues); and Dimarchi et al, EP 0204480 (>34 residues).

Other type of compounds useful in the present invention include analogs or homologs of LHRH which display potent LH releasing activity or inhibit the activity of LHRH; analogs or homologs of HP5 which possesses hematopoetic activity; analogs or homologs of endothelin which possess hypotensive activity; analogs or homologs of enkephalin which have antinociceptive activity; analogs or homologs of chlorecystokinin; analogs or homologs of cyclosporin A which have immunosuppressive activity; analogs or homologs of atrial natriuretic factor; peptidergic antineoplastic agents; analogs or homologs of gastrin releasing peptide; analogs or homologs of somatostatin; gastrin antagonists; bradykinin antagonists; neurotensin antagonists; bombesin antagonists; oxytocin agonists and antagonists; vasopressin agonists and antagonists; hirudin analogs and homologs; analogs and homologs of the cytoprotective peptidecyclolinopeptide; alpha MSH analogs; analogs, and homologs of MSH releasing factor (Pro-Leu-Gly-NH.sub.2); peptides which inhibit collagenase; peptides which inhibit elastase, peptides which inhibit renin; peptides which inhibit HIV protease; peptides which inhibit angiotensin converting enzyme; peptides which inhibit chymases and tryptases and peptides which inhibit blood coagulation enzymes.

Other suitable drugs include non-peptide therapeutic agents such as antibiotics, antimicrobial agents, antineoplastic agents, cardiovascular and renal agents, such as captopril, anti-inflammatory, immunosuppressive and immunostimulatory agents and CNS agents.

Formulations

The combination immediate/delayed release formulation of the present invention can be administered to various mammalian species, such as dogs, cats, humans, etc., in need of such treatment.

The system of the invention can be incorporated in a conventional systemic dosage form, such as a tablet or capsule. The above dosage forms may also include the necessary physiologically acceptable carrier material, excipient, lubricant, buffer, antibacterial, bulking agent (such as mannitol), anti-oxidants (ascorbic acid or sodium bisulfite) or the like.

The dose administered may be carefully adjusted according to the age, weight, and condition of the patient, as well as the route of administration, dosage form and regimen, and the desired result. In general, the dosage forms of formulation containing remogliflozin etabonate or salt thereof (whether by itself or with another antihyperglycemic agent and/or a hypolipidemic agent and/or an antiobesity agent) described above may be administered in amounts as described for remogliflozin etabonate hydrochloride previously The combination of the remogliflozin etabonate or salt thereof and the other antihyperglycemic agent and/or hypolipidemic agent and/or antiobesity agent may be formulated separately or, where possible, in a single formulation employing conventional formulation procedures.

The various formulations of the invention may include one or more fillers or excipients in an amount within the range of up to about 90% by weight and particularly from about 1 to about 80% by weight such as lactose, sugar, corn starch, modified corn starch, mannitol, sorbitol, inorganic salts such as calcium carbonate and/or cellulose derivatives such as wood cellulose and microcrystalline cellulose (also referred to as a compression aid).

One or more binders may be present in addition to or in lieu of the fillers in an amount within the range of from about 0 to about 35% and particularly from about 0.5 to about 30% by weight of the composition. Examples of such binders which are suitable for use herein include polyvinylpyrrolidone (molecular weight ranging from about 5000 to about 80,000 and particularly about 40,000), lactose, starches such as corn starch, modified corn starch, sugars, gum acacia and the like as well as a wax binder in finely powdered form (less than 500 microns) such as carnauba wax, paraffin, spermaceti, polyethylenes or microcrystalline wax.

Where the composition is to be in the form of a tablet, it may include one or more tableting lubricants in an amount within the range of from about 0.2 to about 8% such as from about 0.5 to about 2% by weight of the composition, such as magnesium stearate, stearic acid, palmitic acid, calcium stearate, talc, carnauba wax and the like. Other conventional ingredients which may optionally be present include preservatives, stabilizers, anti-adherents or silica flow conditioners or glidants, such as Syloid brand silicon dioxide as well as FD&C colors.

Tablets of the invention may also optionally include an optional coating layer which may comprise up to about 15% by weight of the tablet composition. The coating layer (which may actually contain the immediate release active) which may be applied over the immediate release solid phase containing particles of delayed release solid phase embedded therein may comprise any conventional coating formulations and will include one or more film-formers or binders, such as a hydrophilic polymer like hydroxypropylmethylcellulose, and/or a hydrophobic polymer like methacrylic acid esters neutral polymer, ethyl cellulose, cellulose acetate, polyvinyl alcohol-maleic anhydride copolymers, .beta.-pinene polymers, glyceryl esters of wood resins and the like and one or more plasticizers, such as triethyl citrate, diethyl phthalate, propylene glycol, glycerin, butyl phthalate, castor oil and the like. Both core tablets as well as coating formulations may contain aluminum lakes to provide color.

The film formers are applied from a solvent system containing one or more solvents including water, alcohols like methyl alcohol, ethyl alcohol or isopropyl alcohol, ketones like acetone, or ethylmethyl ketone, chlorinated hydrocarbons like methylene chloride, dichloroethane, and 1,1,1-trichloroethane.

Where a color is employed, the color may be applied together with the film former, plasticizer and solvent compositions or may be a totally separate top layer.

Figure 4:
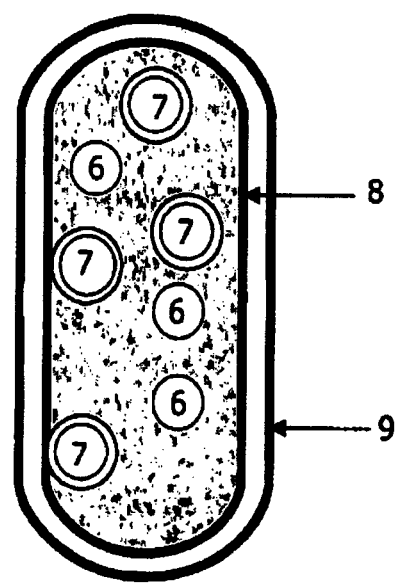
FIG. 4 is a cross sectional representation of a capsule of the pharmaceutical composition described herein.

Capsules of the invention, such as depicted in FIG. 4 may include an excipient or pharmaceutically acceptable carrier interior into which are suspended immediate and delayed release particles. The phrase "pharmaceutically acceptable carrier" as used herein means a pharmaceutically acceptable material, composition or vehicle, such as a liquid or solid filter, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

Capsule formulations may include typical excipients to be added to a capsule including, but not limited to: fillers such as microcrystalline cellulose, soy polysaccharides, calcium phosphate dihydrate, calcium sulfate, lactose, sucrose, sorbitol, or any other inert filler. In addition, there can be flow aids such as fumed silicon dioxide, silica gel, magnesium stearate, calcium stearate or any other materials that impart good flow properties. A lubricant can also be added if desired, such as polyethylene glycol, leucine, glyceryl behenate, magnesium stearate or calcium stearate.

The formulations can conveniently be presented in unit dosage form and can be prepared by any of the methods well known in the art of pharmacy. All methods include bringing into association the drug with the carrier or diluent which constitutes one or more accessory ingredients. In general, the formulations are prepared by uniformly and intimately bringing into association the agent with the carriers and then, if necessary, dividing the product into unit dosages thereof. It will be understood by those skilled in the art that any vehicle or carrier conventionally employed and which is inert with respect to the active agent, and preferably does not interfere with bioadhesion in embodiments employing a bioadhesive coating, may be utilized for preparing and administering the pharmaceutical compositions of the present invention. Illustrative of such vehicles and carriers are those described, for example, in Remington's Pharmaceutical Sciences, 18th ed. (1990), the disclosure of which is incorporated herein by reference.

Specific examples of carriers and diluents include pharmaceutically accepted hydrogels such as alginate, chitosan, methylmethacrylates, cellulose and derivatives thereof (microcrystalline cellulose, hydroxypropyl cellulose, hydroxypropyl methyl cellulose, carboxymethylcellulose, ethylcellulose), agarose and POVIDONE™, kaolin, magnesium stearate, starch, lactose, sucrose, density-controlling agents such as barium sulfate and oils, dissolution enhancers such as aspartic acid, citric acid, glutamic acid, tartaric acid, sodium bicarbonate, sodium carbonate, sodium phosphate, glycine, tricine, tromethamine, and TRIS.

It will be recognized by one of skill in the art that the amount of drug required for therapeutic effect on administration will, of course, vary with the agent chosen, the nature and severity of the condition and the animal undergoing treatment, and is ultimately at the discretion of the physician. Furthermore, the optimal quantity and spacing of individual dosages of a drug will be determined by the nature and extent of the condition being treated, the form, route and site of administration, the particular patient being treated and that such optima can be determined by conventional techniques. It will also be appreciated that the optimal course of treatment, this is, the number of doses given, can be ascertained by those skilled in the art using conventional course of treatment determination tests.

Remogliflozin etabonate may be administered once daily in an amount of at least about 200 mg, particularly from about 250 mg to 500 mg in one solid form such as a tablet or one capsule.

In addition, in accordance with the present invention, the immediate/delayed release remogliflozin etabonate formulation of the invention attains plasma-remogliflozin etabonate concentration (Cmax) by at least one hour, and increases time to reach maximum remogliflozin etabonate plasma concentration (Tmax) by at least about 3 hours (but ranging from 2-4 hours), while having a modest effect on area under the plasma-remogliflozin etabonate concentration time curve (AUC). Thus, the immediate/delayed release remogliflozin etabonate formulation of the invention can be employed for once daily dosing of remogliflozin etabonate in the treatment of diabetes.

Drawings

FIG. 1 provides tablet 18 of the invention, which may be characterized by 3 separate particular embodiments. Tablet 18 may be provided with a homogeneous layer of immediately released first pharmaceutically active ingredient 22, discrete particles of delayed release first pharmaceutically active ingredient 23, a delayed release binder 20, and discrete particles of a second pharmaceutically active ingredient 24, which in this case are delayed release in view of their inclusion in the binder 20.

Alternatively and second, tablet 18 may be provided with an immediate release layer 22 of a second active, discrete delayed release particles of delayed release first pharmaceutically active ingredient 23, an immediate release binder 20, and discrete particles of the first active 24.

Thirdly, tablet 18 may be provided with a color layer 22, discrete delayed release particles of a delayed release first active 23, an immediate release binder 20, and immediate release particles of the first active 24.

Figure 2:
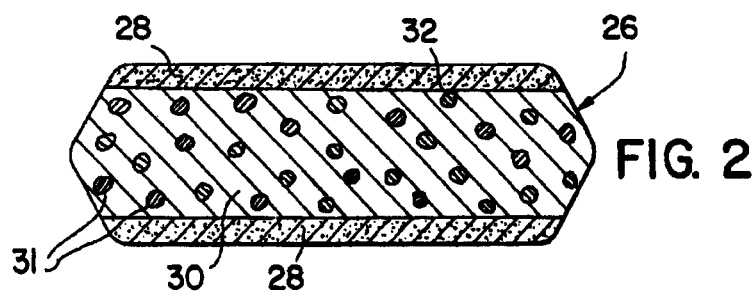
FIG. 2 is a cross sectional representation of a second embodiment of a tablet of the pharmaceutical composition described herein.

FIG. 2 may be characterized by two embodiments. First, tablet 26 may be provided with immediate release homogeneous layers 28 of the first active, discrete particles of the delayed release first active 31, a delayed release binder 30, and discrete particles of a second active 32.

Alternatively and second, tablet 26 may be provided with an immediate release homogeneous layer of the first active 28 as well as immediate release particles of the first active 32. The delayed release first active is provided as delayed release discrete particles 31 in an immediate release binder 30.

Figure 3:
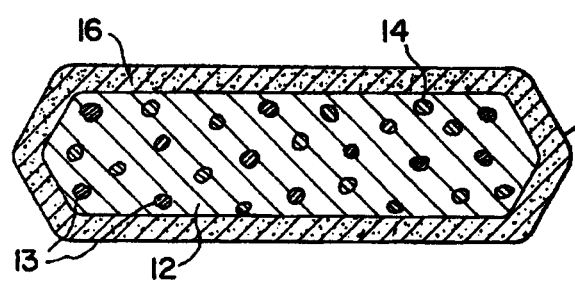
FIG. 3 is a cross sectional representation of a third embodiment of a tablet of the pharmaceutical composition described herein.

FIG. 3 may be characterized by two embodiments. First, tablet 10 may comprise a coating layer 16 completely covering a solid core 12, wherein the layer 16 is a homogeneous immediate release formulation of the first active. Disposed within the core 12 are particles 13 of a delayed release first active and delayed release second active particles 14.

Alternatively and second, tablet 10 may comprise a coating layer 16 which dissolves rapidly upon ingestion. Disposed within layer 16 is an immediate release binder 12 and discrete particles 13 of immediate release first active and discrete particles 14 of a delayed release formulation of the first active.

FIG. 4 may be characterized by two embodiments. First, a gelatin capsule or caplet 9 may contain an interior portion 8 comprising immediate release beads/pellets/particles 6 and controlled/delayed/sustained released beads/pellets/particles 7. Each of such beads 6 and 7 are discrete entities with a first or a first and a second pharmaceutical ingredient. The remaining interior 8 of capsule 9 comprises an excipient or carrier which may be solid or a flowing solid to carry beads 6 and 7.

Alternatively and second, capsule or caplet 9 may contain an interior portion 8 comprising a homogeneous mixture of the first pharmaceutically active ingredient for immediate release upon ingestion. Also contained within the matrix of 8 are two separate beads/pellets/particles 6 and 7 of the active ingredient which release at times different from each other. For example, bead 6 may release with a Tmax about 2-3 hours after ingestion while pellet 7 may release about 4-5 hours after ingestion. Thus, capsule 9 may have 3 separate and distinct formulations of remogliflozin etabonate to thereby achieve a blood concentration of remogliflozin of at least about 50 nanograms/ml over a period of at least about 5 hours.

In all of the above descriptions of FIGS. 1, 2, 3 and 4, the first pharmaceutically active ingredient is remogliflozin etabonate or a salt thereof. The second active, if present, is selected as described herein. Further, the descriptions of a second active can readily be modified by eliminating the second active entirely.

REFERENCE EXAMPLE 1

Remogliflozin etabonate is the pro-drug of remogliflozin (also known as GSK189074), the active entity that inhibits the sodium dependent glucose transporter 2 (SGLT2). However, the short half-life of remogliflozin (approximately 1.5 to 2 h) will likely necessitate twice-daily dosing to be effective. A clinical study was performed to determine whether one of several modified/sustained (MR) release formulations would prolong the pharmacodynamic (PD) effect over the dosing interval and therefore permit a lower total daily dose with twice-daily administration than the dose required with the IR formulation. There was little expectation that any of the MR formulations would provide an opportunity for once daily dosing (Table 1).

TABLE 1

Effect of modified release formulation on PK parameters of GSK189075

| Treatment | N | AUC(O-oo)[1] (ng · h/mL) | AUC(O-t)[1] (ng · h/mL) | Cmax[1] (ng/mL) | tmax[2] (h) | t[1] (h) | T100[3] (h) | AUC Ratio[1,4] |
|---|---|---|---|---|---|---|---|---|
| AA | 25 | 1441 (32.1) | 1433 (32.3) | 574 (39.8) | 1.02 (0.5-3.0) | 1.50 (22.4) | 4.18 (2.8-5.8) | 50.4 (43.8) |
| BB | 27 | 2028 (30.9) | 2019 (30.9) | 892 (28.1) | 1.00 (0.5-2.5) | 1.56 (17.8) | 4.71 (3.2-6.4) | 45.3 (52.4) |
| CC | 30 | 1319 (37.8) | 1304 (38.0) | 365 (52.7) | 4.02 (0.8-6.0) | 1.48 (32.1) | 4.99 (2.1-9.3) | 99.2 (98.3) |
| DD | 31 | 1262 (37.6) | 1252 (37.7) | 319 (40.7) | 2.5 (1.0-6.0) | 1.45 (17.9) | 5.05 (3.5-7.7) | 75.1 (44.6) |
| EE | 28 | 1144 (39.4) | 1129 (39.2) | 409 (51.1) | 5.00 (2.0-10.0) | 1.59 (31.9) | 3.85 (2.5-6.6) | 95.5 (67.5) |
| FF | 28 | 1237 (34.9) | 1228 (35.1) | 374 (43.8) | 2.5 (0.8-4.0) | 1.49 (20.9) | 4.49 (2.7-6.4) | 67.4 (33.8) |

[1]Geometric mean (% CVb)
[2]Median (Range)
[3]Mean (Range)
[4]Ratio of AUC(O -< XI)of GSK189074 over AUC(O-oo)of GSK189075
Treatment AA: GSK189075, 200 mg IR oral tablet
Treatment BB: GSK189075, 250 mg IR oral tablet
Treatment CC: DiffCORE oral tablet with an IR coating of GSK189075, 200 mg
Treatment DD: Bilayer matrix oral tablet containing GSK189075, 200 mg
Treatment EE: GSK189075, 200 mg enteric pellets in an oral capsule
Treatment FF: GSK189075, 200 mg enteric granules in an oral tablet

REFERENCE EXAMPLE 2

Clinical studies already performed suggest that remogliflozin etabonate is only absorbed in the upper GI tract (Table 2). Following oral administration of remogliflozin etabonate in the immediate release IR formulation, the parent drug was rapidly absorbed and converted to remogliflozin, the active entity. Similarly, remogliflozin etabonate was rapidly absorbed and converted to remogliflozin when either the bioenhanced solution or suspension formulation of remogliflozin etabonate was administered directly to the mid-small intestine. However, limited absorption of remogliflozin etabonate and/or conversion to remogliflozin was observed when either the bioenhanced solution or suspension formulation was administered directly to the cecum/colon.

Based on the tmax values, the rate of appearance of remogliflozin etabonate and remogliflozin in the systemic circulation was comparable between all treatments, although a slight delay in tmax of remogliflozin was observed in two subjects when the suspension was administered to the cecum/colon. Using the IR oral tablet of remogliflozin etabonate as the reference treatment, the extent of bioavailability of the active compound, remogliflozin, as determined by AUC (0-infinity) or AUC (0-last), was about 4% or 12% lower when the bioenhanced solution or the suspension formulation was administered directly to the mid-small intestine, respectively; and was about 83% or 96% lower when the solution or suspension was administered directly to cecum/colon, respectively. The extent of bioavailability of remogliflozin was slightly lower (8%) when the suspension as compared to the bioenhanced solution was administered to mid-small intestine; but significantly lower (80%) when the suspension as compared to the bioenhanced solution was administered to cecum/colon. Among all treatments, the IR tablet administered orally had the highest extent of bioavailability of remogliflozin and the suspension administered to cecum/colon had the lowest extent of bioavailability of remogliflozin.

These data indicate that orally administered remogliflozin etabonate is extensively and primarily absorbed from and/or converted to remogliflozin in mid-small intestine, with little absorption and/or metabolic conversion to remogliflozin in cecum/colon. The metabolite to parent AUC ratio was much smaller when remogliflozin etabonate formulations were directly delivered to cecum/colon, as compared to oral IR tablet or drug delivery to mid-small intestine. Using the IR table as the reference, remogliflozin etabonate cmax was about 22% or 40% lower when the bioenhanced solution or the suspension formulation was administered directly to mid-small intestine, respectively; and was about 82% or 96% lower when the solution or suspension was administered directly cecum/colon, respectively.

Remogliflozin etabonate has intrinsically poor permeability in the lower portion of the gastrointestinal tract leading to absorption almost exclusively in the upper part of the gastrointestinal tract. It also has a short half-life (t½=1.5 hrs). This can lead to difficulty in providing release of the required amount of compound during the three major meals and subsequent glucose plasma excursions.

Since remogliflozin has poor permeability in the lower gastrointestinal tract, thus, one would see absorption almost exclusively in the upper gastrointestinal tract. This window of absorption ranges from 3 to 6 hours depending upon food intake, individual differences, etc. Remogliflozin also has a short half-life (t=1.5 hrs). To address these issues, tablets produced according to Examples 1a through 1j release of an IR low dose and a DR high dose of drug to achieve an exposure profile that will maximally inhibit the SGLT2 during the three major glucose excursions (breakfast, lunch and dinner) but minimize the compound exposure during the sleep period. Thus, Example 1c is a compressed tablet of about 350 mg comprising an IR formulation to allow a maximum remogliflozin plasma concentration of 160 ng/mL 1 hr post-ingestion. This Cmax would clear from the plasma to 40 ng/mL after 3 hrs. At that time, the DR formulation, which increases the Tmax from ingestion to 4-5 hrs, would release 250 mg of the active to a Cmax of 450 ng/mL and then clear to a plasma level around 10 ng/mL around 10 PM.

Remogliflozin etabonate, microcrystalline cellulose and croscarmellose sodium are granulated with a water/povidone solution. The granule is dried and milled, then blended with mannitol, microcrystalline cellulose, and croscarmellose. The blend is lubricated with magnesium stearate and compressed.

Enteric coated drug layered pellets are manufactured by coating microcrystalline cellulose spheres with an aqueous suspension containing micronized remogliflozin etabonate, povidone, and purified water, followed by an aqueous Opadry suspension, followed by an aqueous entereic sus-

TABLE 2

Analysis of regional absorption of GSK189074

| Treatment | Single-Dose, 100 mg, GW189075 Administration |
|---|---|
| A | Immediate release tablet taken orally |
| B | Suspension to mid-small intestine |
| C | Bioenhanced solution to the mid-small intestine |
| D | Bioenhanced solution to cecum/colon |
| E | Suspension to cecum/colon |

| GSK189074 PK Parameter | Treatment A | Treatment B | Treatment C | Treatment D | Treatment E |
|---|---|---|---|---|---|
| AUC(0-∞) (hr * ng/mL) | n = 8<br>471 (38) | n = 8<br>416 (41) | n = 8<br>452 (28) | n = 7<br>113 (65) | n = 4<br>37.8 (52) |
| AUC(0-last) (hr * ng/mL) | n = 8<br>463 (39) | n = 8<br>409 (42) | n = 8<br>444 (29) | n = 8<br>75.6 (158) | n = 7<br>16.0 (139) |
| Cmax (ng/mL) | n = 8<br>317 (35) | n = 8<br>192 (65) | n = 8<br>250 (36) | n = 8<br>55.6 (123) | n = 7<br>9.45 (83) |
| tmax (hr) | n = 8<br>0.88 (0.50-1.00) | n = 8<br>0.63 (0.25-1.00) | n = 8<br>0.75 (0.50-1.50) | n = 8<br>0.88 (0.50-1.50) | n = 7<br>0.50 (0.25-2.00) |
| t½ (hr) | n = 8<br>1.35 (8) | n = 8<br>1.25 (8) | n = 8<br>1.27 (9) | n = 7<br>1.13 (16) | n = 4<br>1.92 (45) |
| M/P AUC Ratio 189074/189075 | n = 8<br>99.0 (60) | n = 7<br>73.2 (69) | n = 8<br>33.2 (55) | n = 7<br>14.6 (44) | n = 4<br>8.64 (99) |

EXAMPLE 1

Remogliflozin etabonate capsules (Immediate Release/Delayed release) Various concentrations of remogliflozin etabonate are formulated according to the following Table 3 to result in capsules containing from 250 to 500 mg of the active ingredient per capsule:

TABLE 3

| Immediate release formulation | Delayed release formulation | Excipient |
|---|---|---|
| 50 mg | 200 mg | 100 mg |
| 100 mg | 200 mg | 150 mg |
| 50 mg | 250 mg | 100 mg |
| 100 mg | 250 mg | 150 mg |
| 50 mg | 300 mg | 150 mg |
| 100 mg | 300 mg | 200 mg |
| 50 mg | 350 mg | 200 mg |
| 100 mg | 350 mg | 200 mg |
| 50 mg | 400 mg | 200 mg |
| 100 mg | 400 mg | 200 mg | pension of methacrylic acid copolymer, glycerol monostearate, polysorbate 80, triethyl citrate, and purified water. The formulation is manufactured by standard procedures and uses conventional excipients.

The 50 and 100 mg IR formulated pellets will each be mixed with 200, 250, 300, and 400 mg enteric coated pellets (DR formulation) quantities and filled into hypromellose (hydroxypropylmethyl cellulose or HPMC) capsule shells. Alternatively, the IR and DR formulated pellets may be pressed into tablets as set forth in Example 2.

EXAMPLE 2

Remogliflozin etabonate tablets (Immediate Release/Delayed Release) Various concentrations of remogliflozin etabonate are formulated and pressed into tablets according to the following Table 4 to result in immediate release/delayed release tablets each containing from 350 to 700 mg of ingredients, including the active ingredient:

TABLE 4

| Immediate release formulation | Delayed release formulation | Excipient |
|---|---|---|
| 50 mg | 200 mg | 100 mg |
| 100 mg | 200 mg | 150 mg |
| 50 mg | 250 mg | 100 mg |
| 100 mg | 250 mg | 150 mg |
| 50 mg | 300 mg | 150 mg |
| 100 mg | 300 mg | 200 mg |
| 50 mg | 350 mg | 200 mg |
| 100 mg | 350 mg | 200 mg |
| 50 mg | 400 mg | 200 mg |
| 100 mg | 400 mg | 200 mg |

The new formulations of the invention thus represent a significant advance in the once-a-day administration of remogliflozin etabonate to humans in the treatment of diabetes.

The remogliflozin etabonate formulations described in the aforesaid Examples may be administered once daily as described above, in one, two or more tablets and/or capsules to provide optimal therapeutic control.

The present invention includes combinations of aspects and embodiments, as well as particular embodiments, as herein described throughout the present specification.

Unless stated otherwise, the fact that a particular term or phrase is not specifically defined should not be correlated to indefiniteness or lacking clarity, but rather terms herein are used within their ordinary meaning. When trade names are used herein, applicants intend to independently include the tradename product and the active pharmaceutical ingredient(s) of the tradename product.

The specific pharmacological responses observed may vary according to and depending on the particular active compound selected or whether there are present pharmaceutical carriers, as well as the type of formulation and mode of administration employed, and such expected variations or differences in the results are contemplated in accordance with practice of the present invention.

Although specific embodiments of the present invention are herein illustrated and described in detail, the invention is not limited thereto. The above detailed descriptions are provided as exemplary of the present invention and should not be construed as constituting any limitation of the invention. Modifications will be obvious to those skilled in the art, and all modifications that do not depart from the spirit of the invention are intended to be included with the scope of the appended claims.

What is claimed is:

1. A heterogeneous two phase system comprising:
   (1) a solid phase consisting of
      (a) remogliflozin etabonate or a salt thereof, and
      (b) an immediate release material consisting of
         i. one or more hydrophilic polymers,
         ii. one or more hydrophobic polymers,
         iii. one or more hydrophobic materials selected from one or more of more waxes, fatty alcohols, fatty esters, or any combination thereof; and
   (2) a solid particulate phase consisting of
      (a) remogliflozin etabonate or a salt thereof, and
      (b) a delayed release material consisting of
         i. one or more hydrophilic polymers,
         ii. one or more hydrophobic polymers,
         iii. one or more hydrophobic materials selected from one or more of more waxes, fatty alcohols, fatty esters, or any combination thereof;
   wherein the solid particulate phase of (2) is dispersed throughout and embedded in the solid phase formulation of (1).

2. The heterogeneous two phase system of claim 1, wherein the system provides for a dosing regimen of once daily, wherein the combined amount of remogliflozin etabonate, or a salt thereof, contained in the delayed and immediate release solid phase formulations is from 5 mg to 500 mg.

3. The heterogeneous two phase system of claim 1 wherein the solid particulate phase of (2) is in the form of discrete individual particles or granules and the solid phase of (1) is a matrix.

4. The heterogeneous two phase system of claim 1 wherein the ionic polymer is hydrophilic, and the non-ionic polymer is hydrophilic.

5. The heterogeneous two phase system of claim 1, wherein the one or more hydrophilic polymers are selected form hydroxypropylmethycellulose, hydroxypropyecellulose, polyethylene oxide, carbomer, a methacrylic acid-derived polymer, sodium alginate, or a combination thereof;
   one or more hydrophobic polymers are selected from ethyl cellulose, a polymeric methacrylic acid ester, cellulose acetate butyrate, poly (ethylene-co-vinyl-acetate), or any combination thereof.

6. The heterogeneous two phase system of claim 3, wherein the particles or granules have a mean size from about 30 μm to about 1000 μm.

7. A dosage form comprising a pharmaceutical formulation of claim 1.

8. A dosage form comprising a pharmaceutical formulation of claim 5.

9. A method for preparing a dosage form of the heterogeneous two phase system of claim 1, comprising:
   (A) combining remogliflozin etabonate or a pharmaceutically acceptable salt thereof, and an ionic polymer to form a solid phase delayed release formulation;
   (B) combining remogliflozin etabonate or a pharmaceutically acceptable salt thereof, and a non-ionic polymer to form a solid phase immediate release formulation; and
   dispersing and embedding (A) in (B).

* * * * *